United States Patent [19]

Neti et al.

[11] 4,081,247
[45] Mar. 28, 1978

[54] METHOD AND APPARATUS FOR THE CHEMILUMINESCENT DETECTION OF HCL

[75] Inventors: Radhakrishna Murty Neti; Carl Nelson Cederstrand, both of Brea, Calif.

[73] Assignee: Beckman Instruments, Inc., Fullerton, Calif.

[21] Appl. No.: 654,442

[22] Filed: Feb. 2, 1976

[51] Int. Cl.$^2$ .................. G01N 21/22; G01N 21/52; G01N 25/20
[52] U.S. Cl. .................. 23/232 E; 23/230 PC; 23/253 PC; 23/254 E
[58] Field of Search ............ 23/232 R, 232 E, 254 E, 23/230 PC, 253 PC

[56] References Cited

U.S. PATENT DOCUMENTS

| | | | |
|---|---|---|---|
| 3,627,420 | 12/1971 | Crider | 23/232 E X |
| 3,692,485 | 9/1972 | Neti | 23/232 E X |
| 3,748,097 | 7/1973 | Lerner | 23/232 E |
| 3,835,322 | 9/1974 | Komatsu | 23/232 E X |
| 3,881,869 | 5/1975 | Neti | 23/232 E X |
| 3,904,371 | 9/1975 | Neti | 23/232 R |
| 3,963,928 | 6/1976 | Zolner | 23/254 E X |
| 3,967,933 | 7/1976 | Etess | 23/254 E X |
| 3,973,914 | 8/1976 | Van Heusden | 23/254 E |
| 3,975,159 | 8/1976 | Van Heusden | 23/232 E |
| 3,977,831 | 8/1976 | Fletcher | 23/232 E |
| 3,984,688 | 10/1976 | Von Bargen | 23/254 E |

Primary Examiner—Sidney Marantz
Attorney, Agent, or Firm—Robert J. Steinmeyer; Donald A. Streck

[57] ABSTRACT

A method of measuring trace level hydrogen chloride concentration in a gas stream is disclosed. The gas stream containing hydrogen chloride is passed through a heated vitreous carbon catalyst and then mixed with ozone in a point source reaction chamber. The light emitted in the chemical reaction is measured by a sensitive amplifier and the output is displayed on a meter, recorder, or any other suitable device. Apparatus for measuring trace level hydrogen chloride concentration in a gas stream is also disclosed.

11 Claims, 1 Drawing Figure

4,081,247

METHOD AND APPARATUS FOR THE CHEMILUMINESCENT DETECTION OF HCL

BACKGROUND OF THE INVENTION

The present invention relates to methods and apparatus for detection of hydrogen halide and more particularly to the measurement of hydrogen chloride in trace amounts in a gas stream by chemiluminescent techniques.

Hydrogen chloride is identified as one of the trace constituents in both the upper and lower atmosphere. The identification has been done by various techniques such as theoretical modeling of the upper atmosphere, by solar radiometry, or collecting samples in the stratosphere and bringing them to the ground laboratory for analysis. This is extremely cumbersome and does not offer real time data required to construct better models of the atmospheric reactions. An additional problem is the concentration levels to be measured. The concentrations are suggested to be in the range of $10^8$ to $10^9$ molecules/cc which requires methods and apparatus capable of extremely sensitive measurements.

Chemiluminescent techniques possess the advantage of having a wide dynamic range and are useful for monitoring certain trace samples at the parts per billion level. Older chemiluminescent techniques had certain disadvantages. They required a very high vacuum, careful and precise control of the working pressure, and efficient light collection and collimating systems. In U.S. Pat. No. 3,692,485 to Neti and Bing, which is assigned to the same assignee as this application, there is described an improved method and apparatus for the chemiluminescent detection and measurement of nitric oxide which overcame these disadvantages of prior chemiluminescent techniques. The point source reaction chamber apparatus described in that patent has been incorporated into the present apparatus and makes the method of measurement of hydrogen chloride disclosed herein possible.

SUMMARY OF THE INVENTION

In searching for a method of detection of hydrogen chloride, a diluted HCl vapor for testing was prepared by adding a measured volume of HCl vapor into a plastic bag and blending it with a metered volume of breathing quality air from a cylinder. This test mixture was drawn through a Beckman Model 952 NO/$NO_x$ analyzer, incorporating the reaction chamber of U.S. Pat. No. 3,692,485, at a standard flow rate of 1000 cc/min. The instrument showed a response of 54% on the 25 ppm range in the $NO_x$ mode and 5% in the NO mode. These results suggested that the reaction between HCl and $O_3$ results in the emission of light. The light yield, however, is too small to build a sensitive analyzer capable of the desired measurement levels.

Two important discoveries made trace level hydrogen chloride measurable by chemiluminescent techniques. First, if the HCl-air mixture is passed through a hot vitreous carbon catalyst an activated species X* is created which upon reaction with $O_3$ gives off intense light—a result quite unexpected. Second, the optimum temperature of the catalytic conversion is about 400° C. Either increasing or decreasing the converter temperature decreases the intensity of the light signal developed in the subsequent chemiluminescent react between X* and $O_3$. Additionally, it was found that this method can be used to detect other hydrogen halides.

DESCRIPTION OF THE PREFERRED EMBODIMENT

Figure 1:
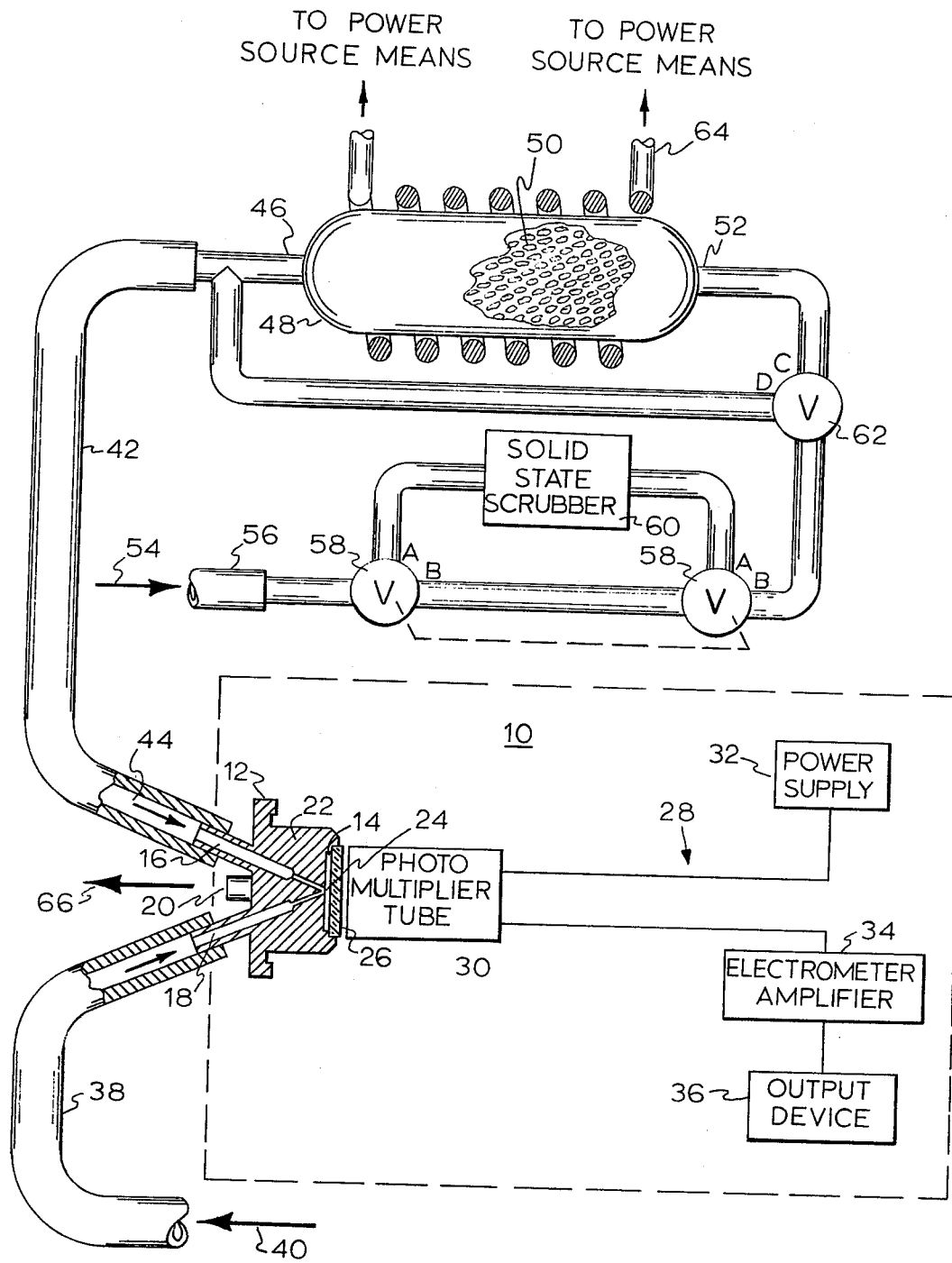
FIG. 1 is a partial cutaway drawing of the apparatus to practice the present invention.

Referring to FIG. 1, chemiluminescent apparatus 10 essentially as described in detail in U.S. Pat. No. 3,692,485 is enclosed by the dotted box and comprises a walled vessel 12 having a reaction chamber 14 therein. The vessel 12 has two inlet passages 16, 18 and an exhaust passage 20 in the wall 22 thereof. As employed in the present invention, the inlet passages are designated as sample inlet passage 16 and $O_3$ inlet passage 18. As can be seen in FIG. 1, the two inlet passages 16, 18, converge together to a common inlet opening 24 into chamber 14.

A light window 26 is positioned in wall 22 of vessel 12 surrounding chamber 14 opposite and in close proximity to common inlet 24 so that light emitted by a chemiluminescent reaction between the gases in the two inlet passages 16, 18, at common inlet 24 can be measured as a point source. Means indicated generally at 28 are associated with the light window 26 for measuring the light emitted by the chemiluminescent reaction.

The measuring means 28 desirably include a photoelectric detector such as photomultiplier tube 30. A power supply 32 such as a battery pack or a connection to generated electrical current is connected to photomultiplier tube 30. A suitable electrometer amplifier 34 is connected to photomultiplier tube 30 for amplifying an electrical signal produced by photomultiplier tube 30 as a result of a chemiluminescent reaction. A suitable output device 36 is connected to amplifier 34 for presenting the amplified signal for evaluation. The output device 36 could be a recorder for making a permanent record for later evaluation, a meter for immediate indication, computer, or other appropriate devices. In particular, when incorporated in an extraterrestrial platform such as a balloon or satellite, the output device 36 could be a telemetering device for sending the results of stratospheric measurement in real time to tracking stations on earth.

To practice the present invention, apparatus as follows is provided in addition to the chemiluminescent apparatus 10 described above. Means are connected to $O_3$ inlet passage 18 such as $O_3$ inlet pipe 38 for supplying $O_3$ gas 40 to $O_3$ inlet passage 18. Means are connected to sample inlet passage 16 such as sample inlet pipe 42 for supplying a sample gas 44 to sample inlet passage 16. Sample supply means such as sample inlet pipe 42 are further connected to sample outlet 46 of conversion chamber 48 containing vitreous carbon 50 and having test gas inlet 52 positioned such that gas entering chamber 48 therethrough and exiting through sample outlet 46 will have to pass through vitreous carbon 50. Vitreous carbon 50 can be of any convenient form such as pellets, rods, etc. Means are connected to test gas inlet 52 for supplying the test gas 54 to conversion chamber 48.

It is well known that NO and $O_3$ will combine to form a chemiluminescent reaction. Likewise, it is known in the prior art that when $NO_x$ is brought in contact with heated vitreous carbon, the $NO_x$ is converted to NO. Thus, if test gas 54 is known or suspected to contain NO and/or $NO_x$, provision must be made to compensate for their presence since any chemiluminescent reaction of the test gas with $O_3$ can be a result of reaction with the converted HCl, any NO, and any converted $NO_x$. As shown in FIG. 1, the apparatus is capable of detecting a hydrogen halide alone or in the presence of NO and/or $NO_x$. The test gas 54 enters test gas pipe 56 which communicates with valves 58. With valves 58 in the "A" position, test gas 54 passes through a solid state scrubber 60 capable of removing the hydrogen halide (such as argentic oxide) and conducts test gas 54 to valve 62. With valves 58 in the "B" position, test gas 54 is ducted directly to valve 62. With valve 62 in the "C" position, test gas 54 is conducted into conversion chamber 48 through test gas inlet 52. With valve 62 in the "D" position, test gas 54 is conducted directly to sample outlet 46 and into sample inlet pipe 42, bypassing the conversion process. As will hereinafter be described, this valving arrangement allows the apparatus to be used for conducting five detections:

1. NO
2. NO + $NO_x$
3. $NO_x$
4. Hydrogen Halide
5. Hydrogen Halide in the presence of NO and/or $NO_x$.

Conversion chamber 48 has heating means 64 disposed adjacent thereto, heating means 64 being connected to an appropriate power source (not shown) e.g. electricity, hot air, steam, to heat the conversion chamber 48 and the vitreous carbon 50 therein to between 300° and 500° C, but ideally, at about 400° C. It is to be understood that $O_3$ inlet pipe 38 and sample inlet pipe 42 are shown as simplified representations of the apparatus comprising the elements of the present invention and that the actual apparatus comprising chemiluminescent apparatus 10 may employ various additional apparatus to accomplish necessary flow rate, volume and metering functions attendant to proper calibrated operation.

To practice the method of detecting a hydrogen halide without the presence of $NO_x$ or NO by the present invention with the apparatus as described above, the test gas 56 containing an unknown quantity of, for example, HCl is introduced into conversion chamber 48 through test gas inlet 52 with valves 58 in the "B" position and valve 62 in the "C" position. Conversion chamber 48 is heated to about 400° C by heating means 64. As the test gas 54 passes through conversion chamber 48, vitreous carbon 50 acts as a catalyst to convert the HCl to an activated species X*. The X* containing sample gas 44 passes from conversion chamber 48 into reaction chamber 14 through sample outlet 46, sample inlet pipe 42, and sample inlet passage 16. Simultaneously, $O_3$ gas 40 is introduced into reaction chamber 14 through $O_3$ inlet pipe 38 and $O_3$ inlet passage 18. At common inlet opening 24 a chemiluminescent reaction takes place the intensity of which is directly proportional to the quantity of HCl in the test gas 54. The chemiluminescently produced light is detected and processed by measuring means 28 in a conventional manner after original calibration according to well known techniques. The reacted gases 66 exit from reaction chamber 14 through exhaust passage 20.

If the sample stream consists of $NO_x$ and/or NO and a hydrogen halide, as for example HCl, the mixture may be analyzed according to the following method:

Step 1—Determine the NO + $NO_x$ + HCl content by sampling with valves 58 in the "B" position and valve 62 in the "C" position.

Step 2—Determine the NO + $NO_x$ content by sampling with valves 58 in the "A" position and valve 62 in the "C" position.

Step 3—Subtract the results of step 2 from those of step 1 to determine HCl by:

$$(NO + NO_x + HCl) - (NO + NO_x) = HCl$$

Additional analysis can be made by:

Step 4—Determine the NO content by sampling with the valves 58 in the "A" position and valve 62 in the "D" position.

Step 5—Determine the $NO_x$ content by subtracting the results of step 4 from those of step 2 by:

$$(NO + NO_x) - NO = NO_x$$

Thus, it can be seen that the apparatus herein disclosed is capable of making the five determinations mentioned earlier.

Having thus described our invention, we claim:

1. The method of measuring the hydrogen halide concentration in a gas stream containing neither NO nor $NO_x$ comprising the steps of:
   (a) bringing the gas stream in contact with heated vitreous carbon;
   (b) mixing the gas stream with ozone; and,
   (c) measuring the intensity of the light emitted as a result of the chemiluminescent reaction whereby the hydrogen halide concentration may be measured.

2. The method of claim 1 wherein said vitreous carbon is heated to about 400° C.

3. The method of claim 1 wherein the hydrogen halide the concentration of which is to be measured is hydrogen chloride.

4. The method of measuring the hydrogen halide concentration in a gas stream containing neither NO nor $NO_x$ comprising the steps of:
   (a) bringing the gas stream in contact with vitreous carbon heated to between 300° and 500° C to convert the hydrogen halide to an activated species;
   (b) mixing the converted gas stream containing the activated species with ozone at the entrance to a reaction chamber so that the mixture enters the reaction chamber as a point source; and,
   (c) measuring the intensity of the light emitted as a result of the chemiluminescent reaction between the ozone and the activated species at the point source whereby the hydrogen halide concentration may be measured.

5. The method of claim 1 wherein said vitreous carbon is heated to about 400° C.

6. The method of claim 5 wherein the hydrogen halide the concentration of which is to be measured is hydrogen chloride.

7. The method of measuring the hydrogen halide concentration in a gas stream containing NO and/or $NO_x$ comprising the steps of:
   (a) bringing the gas stream in contact with vitreous carbon heated to between 300° and 500° C;
   (b) mixing the gas stream with ozone;
   (c) measuring the intensity of the light emitted as a result of the chemiluminescent reaction whereby the concentration of the hydrogen halide and NO and/or $NO_x$ may be measured;
   (d) scrubbing the gas stream to remove the hydrogen halide prior to bringing the gas stream into contact with the heated vitreous carbon and mixing the gas stream with ozone;

(e) measuring the intensity of the light emitted as a result of the chemiluminescent reaction between the ozone and the scrubbed mixture whereby the concentration of the NO and/or $NO_x$ may be measured; and, (f) determining the hydrogen halide concentration as a function of the results of step (c) minus the results of step (e) above.

8. The method of claim 7 wherein the hydrogen halide concentration of which is to be measured is hydrogen chloride.

9. Apparatus for measuring the concentration of a hydrogen halide in a gas stream comprising:
(a) a conversion chamber having inlet means thereto and outlet means therefrom;
(b) vitreous carbon disposed within said conversion chamber;
(c) means for heating said vitreous carbon cooperating with said conversion chamber;
(d) scrubber means for removing hydrogen halide from the gas stream communicating with said inlet means to said conversion chamber;
(e) first valve means cooperating with said inlet means to said conversion chamber and said scrubber means wherein when said first valve means is in a first position the gas stream passes through said scrubber means before entering said conversion chamber and when said first valve means is in a second position the gas stream does not pass through said scrubber means before entering said conversion chamber;
(f) a reaction chamber having a pair of inlets for mixing gases in said reaction chamber and an exhaust passage, one of said inlets being connected to said outlet means of said conversion chamber and the other of said inlets being adapted to be connected to a source of ozone;
(g) a light window positioned in said reaction chamber so that the light emitted by a chemiluminescent reaction between the gases in said inlets can be measured; and,
(h) means associated with said light window for measuring the light emitted by the chemiluminescent reaction.

10. Apparatus as claimed in claim 9 and additionally: second valve means cooperating with said inlet means and said outlet means of said conversion chamber wherein when said second valve means is in a first position the gas stream passes through said conversion chamber and when said second valve means is in a second position the gas stream bypasses said conversion chamber.

11. Apparatus as claimed in claim 9 wherein said scrubber means employs argentic oxide.

* * * * *